(12) United States Patent
Connor

(10) Patent No.: US 7,975,707 B1
(45) Date of Patent: Jul. 12, 2011

(54) DENTAL FLOSS OR TAPE WHOSE CROSS-SECTIONAL SIZE CAN BE ADJUSTED AFTER INSERTION

(75) Inventor: Robert A. Connor, Minneapolis, MN (US)

(73) Assignee: Medibotics LLC, Minneapolis, MN (US)

( * ) Notice: Subject to any disclaimer, the term of this patent is extended or adjusted under 35 U.S.C. 154(b) by 361 days.

(21) Appl. No.: 12/315,539

(22) Filed: Dec. 4, 2008

Related U.S. Application Data

(60) Provisional application No. 61/009,091, filed on Dec. 26, 2007.

(51) Int. Cl.
*A61C 15/00* (2006.01)
*D02G 3/00* (2006.01)

(52) U.S. Cl. .................. 132/321; 428/364; 428/373

(58) Field of Classification Search .......... 132/321–329; 428/364, 373, 397, 399; 606/228–231
See application file for complete search history.

(56) References Cited

U.S. PATENT DOCUMENTS

| 4,142,538 A | 3/1979 | Thornton |
|---|---|---|
| 4,187,390 A | 2/1980 | Gore |
| 4,836,226 A | 6/1989 | Wolak |
| 4,974,614 A | 12/1990 | Selker |
| 4,974,615 A | 12/1990 | Doundoulakis |
| 5,063,948 A | 11/1991 | Lloyd |
| 5,293,886 A | 3/1994 | Czapor |
| 5,316,028 A | 5/1994 | Flemming |
| 5,433,226 A | 7/1995 | Burch |
| 5,682,911 A | 11/1997 | Harada |
| 5,718,251 A | 2/1998 | Gray |
| 5,755,243 A | 5/1998 | Roberts |
| 5,765,576 A | 6/1998 | Dolan |
| 5,775,346 A | 7/1998 | Szyszkowski |
| 5,830,495 A | 11/1998 | Ochs |
| 5,845,652 A | 12/1998 | Tseng |
| 6,003,525 A | 12/1999 | Katz |
| 6,027,592 A | 2/2000 | Tseng |
| 6,039,054 A | 3/2000 | Park |
| 6,112,753 A | 9/2000 | Arsenault |
| 6,123,982 A | 9/2000 | Fontana |
| 6,250,313 B1 | 6/2001 | Rees |
| 6,607,000 B2 | 8/2003 | Marwah |
| 6,672,316 B1 | 1/2004 | Weihrauch |
| 6,742,528 B2 | 6/2004 | Dave |
| 7,017,591 B2 | 3/2006 | Brown |
| 7,025,986 B2 | 4/2006 | Brown |
| 7,055,530 B2 | 6/2006 | Husted |
| 2006/0225764 A1 | 10/2006 | Mark |

*Primary Examiner* — Rachel R Steitz

(57) ABSTRACT

This invention is dental floss or dental tape whose cross-sectional size can be adjusted after it is inserted into the proximal space. This is accomplished by making floss or tape with two or more members, wherein longitudinally pulling a subset of those members relative to the other members increases the cross-sectional size of the floss or tape. The size of the floss can be optimally adjusted to match the size of the interproximal space and clean the space most efficiently.

7 Claims, 2 Drawing Sheets

Figure 3:
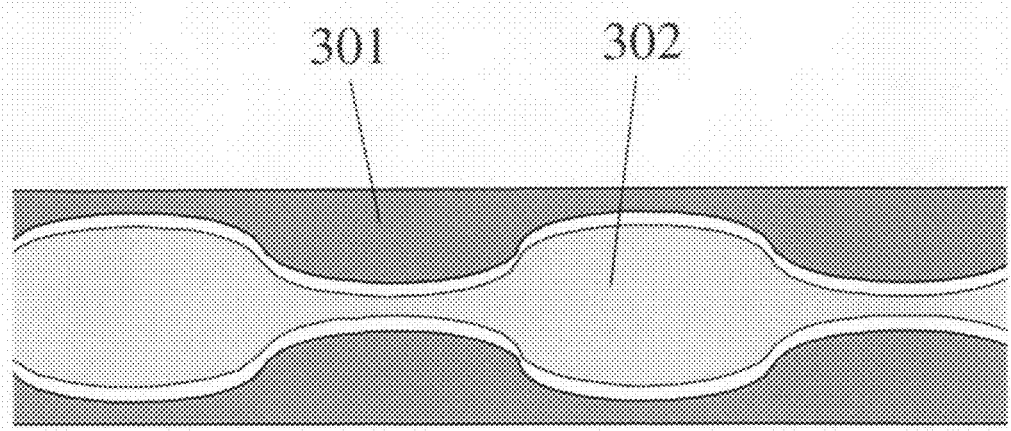

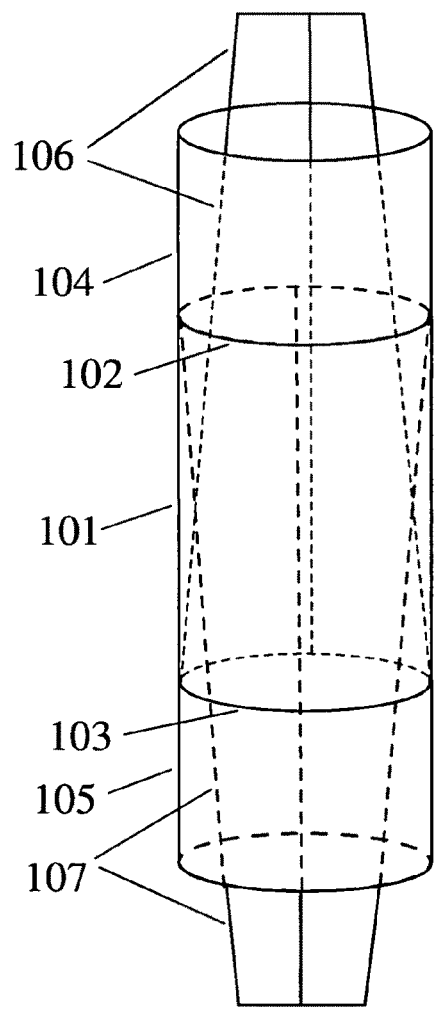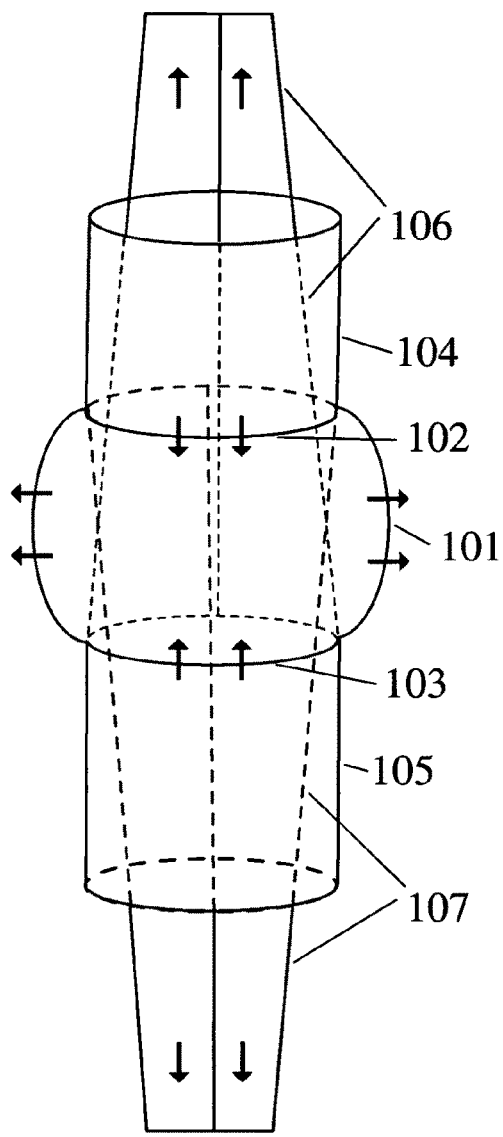
Fig. 1
Fig. 2

DENTAL FLOSS OR TAPE WHOSE CROSS-SECTIONAL SIZE CAN BE ADJUSTED AFTER INSERTION

CROSS-REFERENCE TO RELATED APPLICATIONS

This patent application claims the priority benefit of provisional patent application Ser. No. 61/009,091 entitled "Adjustable dental floss with separable [sic] movement of longitudinal members" filed on Dec. 26, 2007 by Robert A. Connor.

FEDERALLY SPONSORED RESEARCH

Not Applicable

SEQUENCE LISTING OR PROGRAM

Not Applicable

BACKGROUND

1. Field of Invention

This invention relates to cleaning the interproximal spaces between teeth.

2. Prior Art

Dental caries is one of the most common diseases in the world. The gaps between teeth, called interproximal spaces, are some of the most difficult places to clean in order to prevent dental caries. Interproximal spaces can be narrow, especially at the top, making it difficult to insert cleaning devices such as brushes. Thin dental floss and dental tape were created to insert into the narrow top of an interproximal space and clean the space below.

However, floss or tape that is sufficiently thin to insert into the narrow top of the space can be an inefficiently-small tool with which to clean the wider, rounded-wall space below. Often, the floss must be moved back and forth many times in a large number of different angles in order to clean all the rounded surfaces of the wider portion of the interproximal space. Moving the floss back and forth in all of these different angles can be very time consuming and, particularly for teeth toward the back of the mouth, quite cumbersome.

Due to the importance of keeping interproximal spaces clean for prevention of dental caries and the challenges involved with conventional flossing, different approaches to this problem have been pursued in the prior art. However, the ongoing prevalence of dental caries arising from insufficiently-cleaned interproximal spaces is a testimony to the remaining need for better solutions to this problem. The prior art has limitations which are addressed by this current invention. We now discuss the four main approaches to cleaning interproximal spaces in the prior art: interproximal brush; floss with longitudinally-uniform cross-sectional structure; floss with longitudinal variation in cross-sectional structure, and floss with changing cross-sectional structure:

1) Interproximal Brush:

A variety of interproximal brushes are known in the prior art. Brushes have a relatively rigid central core in order to provide sufficient stiffness for insertion into the space and to move the bristles, or other protrusions, back and forth. The bristles or other protrusions generally extend out in a radial and/or perpendicular manner from the central rigid core. The main limitation of interproximal brushes is that a relatively rigid central core is too large to insert into smaller interproximal spaces. Even for larger spaces, a brush may not be able to clean the narrow top portion. Another limitation of brushes is that they are virtually always inserted in one direction, from the outside, and thus do not clean rounded wall surfaces in a symmetric manner. Finally, it can be a challenge to avoid injuring soft mouth tissue with an automated system with a rigid-core brush.

2) Floss with Longitudinally-Uniform Cross-Sectional Structure:

Traditional dental floss has the same general cross-sectional shape throughout its length. Many types of such floss are known in the prior art. Some such floss in the prior art has advanced cross-sectional shapes, textures, abrasiveness, softness, porosity, or elasticity to improve its cleaning ability. For example, see U.S. Pat. Nos. 4,187,390 (Gore), 5,755,243 (Roberts), 5,765,576 (Dolan), 5,830,495 (Ochs), 5,845,652 (Tseng), 6,027,592 (Tseng), 6,039,054 (Park), 6,742,528 (Dave), 7,017,591 (Brown) and 7,025,986 (Brown). However, even advanced longitudinally-uniform floss has limitations. Since the floss must be thin enough to insert through the narrow top of an interproximal space, it often must be moved in a wide range of angles to clean the entire interproximal space, especially when the space is wider at the bottom and teeth on either side are rounded. Moving the floss in such a wide range of angles can be time-consuming and, especially for teeth that are far back in the mouth, can be very cumbersome as well.

3) Floss with Longitudinal Variation in Cross-Sectional Structure:

A variation on traditional dental floss is dental floss with fixed cross-sectional structures at intervals along its length. Such floss can be inserted into the space using a thin section of the floss and then a section of the floss with wider cross-sectional structure can be pulled through the space. Cross-sectional structures can include: cuts or holes as in U.S. Pat. Nos. 4,974,615 (Doundoulakis), 5,293,886 (Czapor), 6,607,000 (Marwah), and 7,055,530 (Husted); longitudinal segments with different diameters or flexibility as in U.S. Pat. Nos. 4,142,538 (Thornton), 4,974,614 (Selker), 5,433,226 (Burch), 5,718,251 (Gray), 7,055,530 (Husted) and 20060225764 (Mark); or protrusions at intervals such as knots, spheres, dimples, bristles, flanges as in U.S. Pat. Nos. 4,836,226 (Wolak), 4,974,615 (Doundoulakis), 5,063,948 (Lloyd), 5,316,028 (Flemming), 5,682,911 (Harada), 5,775,346 (Szyszkowski), 6,003,525 (Katz), 6,112,753 (Arsenault), 6,250,313 (duRees), and 6,672,316 (Weihrauch).

Such floss can reduce the number of angles required to clean an interproximal space compared to longitudinally-uniform floss, but the approach still has limitations. If the cross-sectional protrusions are relatively small and flexible, then a large number of angles is still required to clean a wide space with rounded walls. On the other hand, if the cross-sectional protrusions are relatively large and inflexible, then they may become wedged in the interproximal space or even tear gum tissue. The cross-sectional size of the protruding structures in the prior art can not be adjusted within the interproximal space. The ability to custom adjust cross-sectional size would be desirable to clean interproximal spaces of different sizes.

4) Floss with Changing Cross-Sectional Structure:

For the above reasons, it is desirable to have dental floss or dental tape whose cross-sectional structure can be changed within the interproximal space itself. There has been some, albeit limited, progress toward this goal in the prior art as in U.S. Pat. No. 6,123,982 (Fontana) and (GUM™ Expandable Floss™). The prior art includes dental floss with compressed and/or coated fibers that expand due to friction or chemical reaction (such as exposure to moisture). Floss with this expansion potential is a conceptual advance over traditional floss, but still has limitations. If the floss expands with friction or exposure to moisture, then it may expand prematurely before or during insertion, due to the friction of insertion or moisture on the tops of the teeth.

Also, in the prior art the mass of material in a given cross-sectional slice is not increased, just the volume thereof; thus, it can be difficult to ensure that floss after expansion has sufficient resiliency to thoroughly clean larger spaces. An analogy might help to illustrate this point. Suppose that one has a task that requires moderate abrasive action in a tight space. One might be able to use an unexpanded sponge, coated with a moderately abrasive cleaning powder, for this purpose. However, if one were to expand the volume of the sponge by soaking it in water, then it would be much less resilient for providing the required abrasive action.

The limitations of the prior art may be summarized as follows. Brushes are limited because it is difficult to fit their rigid cores into narrow interproximal spaces or the narrow tops of wider spaces. Traditional floss is limited because of its small diameter relative to the wide, rounded-wall space that it must clean. The many different angles at which traditional floss must be moved to clean the entire space can be time-consuming and, in areas in the back of the mouth, very cumbersome. Floss with fixed cross-sectional structures such as knots, spheres, and bristles are limited because the cross-sectional size of these structures can not be adjusted for different size spaces. Further, protruding cross-sectional structures may become wedged in the interproximal space or even tear gum tissue. Current-generation expandable floss relies on friction or chemical reaction for expansion and may expand prematurely before or during insertion. Also, current-generation expanding floss increases the volume, but not the mass, of material in a given cross-sectional slice. Thus, the expanded floss may not have sufficient resiliency to clean wide spaces. This present invention provides a novel way to clean interproximal spaces that addresses all of these limitations of the prior art.

SUMMARY

The present invention is dental floss or dental tape whose cross-sectional size can be adjusted after it is inserted into the proximal space. This is accomplished by making floss or tape with two or more members, wherein longitudinally pulling a subset of those members relative to the other members increases the cross-sectional size of the floss or tape. This has many advantages over the prior art.

Compared to interproximal brushes, this invention has no rigid core and thus can be used in smaller interproximal spaces. Compared to traditional floss or tape, the expanded cross-sectional size of this floss or tape can clean a wide, rounded-wall interproximal space with far fewer motions. Compared to floss with fixed cross-sectional structures such as knots, spheres, and bristles, the cross-sectional size of this floss or tape can be custom adjusted to optimally fit each interproximal space. In this manner, it less likely to be too big (and thus get stuck) or be too small (and thus require many angles for proper cleaning). Also with respect to possibly getting stuck, some embodiments of this invention allow the user to decrease the cross-sectional size of floss after it has been increased. This can be useful for removing floss if it were to get stuck in the interproximal space. This is another advantage over floss with fixed-size protrusions. If a fixed-size protrusion gets stuck in the interproximal space, it can not be reduced in size to remove it.

Compared to current-generation expanding floss, this present invention allows greater control over expansion. With this present invention, cross-sectional expansion only occurs after insertion when one takes a specific action. Expansion will not happen prematurely due to friction or moisture before or during insertion. Also, with this present invention, the amount of mass in a central cross-sectional slice of floss or tape can be increased as well as its volume. For example, in some embodiments of the present invention, the mass in a given cross-sectional slice is increased due to longitudinal compression. In other embodiments of the present invention, the mass in a given cross-sectional slice is increased due to longitudinal alignment. These features provide greater control over the resiliency of the expanded section for cleaning wider spaces.

DRAWINGS

Introduction

FIGS. 1 and 2 show one embodiment of this invention, but do not limit the generalizability of the claims. FIG. 1 shows a pre-expansion transparent side view of one embodiment of this invention with overlapping strips within a sheath with an oval-shape cross-section. FIG. 2 shows this same view and embodiment, after the cross-sectional size has been expanded in the central section of the sheath by pulling the longitudinal strips.

Figure 4:
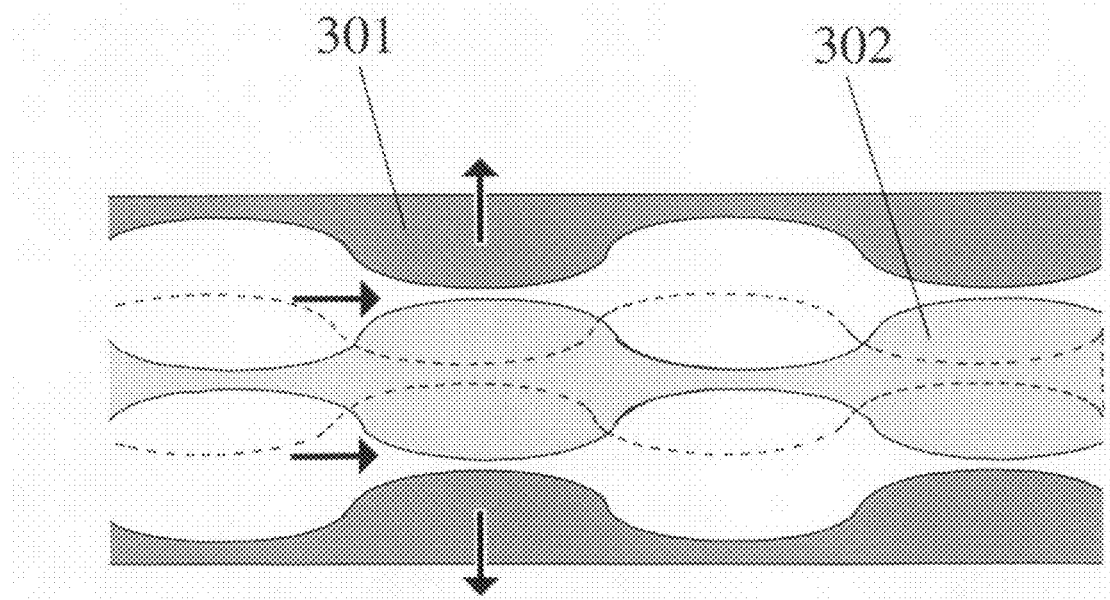

FIGS. 3 and 4 show a second embodiment of this invention, but also do not limit the generalizability of the claims. FIG. 3 shows a pre-expansion transparent side view of one embodiment of this invention with a central core and a flexible outer tube, each with variation in thickness. FIG. 4 shows this same view and embodiment, after the cross-sectional size has been expanded by pulling the core so as to align the thicker areas of the inner core with the thicker areas of the outer tube.

DETAILED DESCRIPTION

FIGS. 1 and 2 show one embodiment of this invention, but do not limit the generalizability of the claims. FIG. 1 shows a transparent side view of one embodiment of this invention before cross-sectional expansion. Specifically, the embodiment in FIG. 1 shows an outer sheath with a central segment 101 and two end segments, 104 and 105. This sheath is made of a flexible or compressible material which may be selected from the group consisting of nylon, PTFE, polyethylene, or another material. In variations on this embodiment, this outer layer may have a cross section which is basically flat or round, rather than oval-' shaped.

FIG. 1 shows two longitudinal strips, 106 and 107, that are partially enclosed by sheath (101, 104, and 105) and partially protrude out of the sheath. These strips may be made of material selected from the group consisting of nylon, PTFE, polyethylene, or another material. These two strips, 106 and 107, overlap within the central portion of the sheath 101. In this embodiment, strip 106 is attached to the sheath along half of the circumference of circle 103 and strip 107 is attached to the sheath along half of the circumference of circle 102. These attachments are on the opposite-side halves of the circles to allow the two strips 106 and 107 to slide past each other when pulled outwards.

In FIG. 1, the central portion of sheath 101 is in a non-expanded configuration so that it may be inserted into the top of the interproximal space. A user holds the end segments of the sheath, 104 and 105, during insertion into the interproximal space so that this non-expanded configuration is maintained during insertion.

FIG. 2 shows this same view and embodiment as in FIG. 1, but after the central portion of the sheath 101 has been inserted into the interproximal space and its cross-sectional size has been expanded. Once the sheath has been inserted into the interproximal space, it is expanded to clean the space more efficiently. Specifically, in FIG. 2, strips 106 and 107 are pulled outwards from the sheath. In this embodiment, the strips are pulled outward manually by a person, but in other embodiments this pulling could be done by an automated flosser.

The outward pulling of strips 106 and 107 causes them to slide past each other where they overlap in the central section 101 of the sheath. Since the strips are attached to the sheath at circles 102 and 103, this pulling and sliding causes circles 102 and 103 to move toward each other. As circles 102 and 103 move toward each other, the central section 101 of the sheath is compressed longitudinally and expanded cross-sectionally. The result of the cross-sectional expansion depends on the material characteristics of the sheath. A relatively thin, but flexible, sheath will likely bunch-up or fold-up into a wrinkled mass. A thicker, but compressible, sheath will likely bulge outwards in a relatively-smooth torus shape. In the embodiment shown in FIG. 2, the center of the sheath 101 is shown bulging outward in a torus shape.

This invention allows adjustable expansion of the floss within the interproximal space after insertion so that expansion can be optimally adjusted to fit the size of the space. With this embodiment, it is also possible to reverse the expansion to further adjust size or to remove the floss if it gets stuck, by letting go of strips (106 and 107) and pulling sheath ends (104 and 105). Intra-proximal space adjustment of the cross-sectional size of dental floss or tape is novel and useful.

FIG. 3 shows a second embodiment of this invention, but also does not limit the generalizability of the claims. FIG. 3 shows a pre-expansion transparent side view of one embodiment of this invention with a central cylindrical core (302) and an elastic outer tube (301), each with sinusoidal variation in thickness. In a pre-expansion configuration, the thicker areas of the central core (302) are aligned with the thinner areas of elastic outer tube (301), so that the cross-sectional size of the elastic tube is minimized for insertion into the interproximal space. After the floss has been inserted into the interproximal space, it is expanded to clean the space more efficiently. FIG. 4 shows this same view and embodiment, but after the cross-sectional size of the elastic outer tube (301) has been expanded by longitudinally pulling the central core (302) so as to align the thicker areas of central core (302) with the thicker areas of elastic outer tube (301).

CONCLUSION

Although considerable progress has been made toward developing ways to clean the interproximal spaces between teeth, the prior art still has many limitations and dental caries based on inadequate cleaning of interproximal spaces remains widespread. This present invention is dental floss or tape whose cross-sectional size can be adjusted by the user after it is inserted into the interproximal space. The size of the floss can be optimally adjusted to match the size of the space and clean the space most efficiently. This is both novel and useful.

This invention has many advantages over the prior art. Compared to interproximal brushes, this invention can clean even small interproximal spaces. Compared to traditional floss or tape, the optimal cross-sectional size of this invention enables cleaning in much less time. Compared to floss with fixed protrusions such as knots, spheres, and bristles, this invention: can be optimally sized to clean each space; is less likely to become stuck; and can be decreased in size for easy removal in the unlikely event that is does become stuck. Compared to compacted floss with a coating that is removed by friction or moisture, this invention will not be expanded prematurely during insertion and offers better control of the resiliency of the expanded floss because it can change the mass of material, not just the volume, in a given cross-sectional slice.

I claim:

1. Dental floss or tape whose cross-sectional size can be adjusted after insertion into the interproximal space, comprising:

Dental floss or tape with two or more members within the same longitudinal segment, wherein one or more of these members can be pulled longitudinally relative to the other member or members and wherein this longitudinal pulling increases the cross-sectional size of the floss or tape, the floss or tape has an inner core member and an outer tube member, each with longitudinal-variation in cross section thickness, wherein pulling one member relative to the other aligns the thicker portions of both and thus increases the cross-section size of the floss or tape.

2. The dental floss or tape in claim 1 wherein the members are largely parallel to each other.

3. The dental floss or tape in claim 1 wherein the members are largely concentric.

4. The dental floss or tape in claim 1 wherein one pattern of pulling members increases the cross-sectional size of the floss or tape and a different pattern of pulling members decreases the cross-sectional size of the floss or tape.

5. The dental floss or tape in claim 1 wherein the members are moved manually by selectively pulling one or more members relative to the other members.

6. The dental floss or tape in claim 1 wherein the members are moved automatically by a device that selectively pulls one or more members relative to the other members.

7. A method of adjusting the cross-sectional size of dental floss or tape after insertion into the interproximal space, comprising:

Longitudinally pulling one or more members within the floss or tape relative the other member or members within the floss or tape, wherein this longitudinal pulling increases the cross-sectional size of the floss or tape, the floss or tape has an inner core member and an outer tube member, each with longitudinal-variation in cross section thickness, wherein pulling one member relative to the other aligns the thicker portions of both and thus increases the cross-section size of the floss or tape.

* * * * *